United States Patent [19]

Glazer et al.

[11] 4,042,637

[45] Aug. 16, 1977

[54] PROCESS OF PURIFYING VINYL CHLORIDE

[75] Inventors: Emmett Jean Glazer, Stow; Edwin Studley Smith, Cuyahoga Falls, both of Ohio

[73] Assignee: The Goodyear Tire & Rubber Company, Akron, Ohio

[21] Appl. No.: 677,642

[22] Filed: Apr. 15, 1976

[51] Int. Cl.$^2$ .............................................. C07C 21/00
[52] U.S. Cl. ............................ 260/652 P; 260/654 S; 260/656 R

[58] Field of Search ......... 260/654 S, 652 P, 656 AC, 260/656 R

[56] References Cited

FOREIGN PATENT DOCUMENTS 661,138   4/1963   Canada .............................. 260/654 S Primary Examiner—Delbert E. Gantz
Assistant Examiner—Joseph A. Boska
Attorney, Agent, or Firm—F. W. Brunner; J. M. Wallace, Jr.

[57] ABSTRACT

The invention relates to a process for purifying vinyl chloride monomer by contacting it with zinc metal.

5 Claims, No Drawings

PROCESS OF PURIFYING VINYL CHLORIDE

This invention relates to a process for purifying monomeric vinyl chloride.

Monomeric vinyl chloride, especially vinyl chloride recovered from a polymerization process, generally contains hydrogen chloride and other impurities. These impurities generally cause a reduction of of polymerization rate and result in the need of larger quantities of initiator to control the polymerization rate. This large quantity of initiator impairs the color of polyvinyl chloride produced therefrom. Consequently it is desirable to purify to eliminate the undesirable effects of these impurities.

According to the prior art vinyl chloride monomer has been purified by passing the monomer over solid pellets of caustic. This method has a disadvantage that pellets of caustic will lump together when exposed to the small amounts of water in the vinyl chloride monomer and this lumping together requires frequent changing of the bed of caustic pellets.

According to the present invention it has been found that vinyl chloride monomer can be purified by treating the monomer with metallic zinc. The zinc used will generally be in the form of small pellets and of a type that will readily react with the impurities in the vinyl chloride.

The following example illustrates the process of this invention.

EXAMPLE 1

One hundred grams of mossy zinc which had been screened through an eight mesh screen was added to a cylinder. Then five pounds of vinyl chloride monomer were added. The cylinder was sealed and shaken periodically to thoroughly contact the zinc with the vinyl chloride monomer. Before treatment with the zinc a sample of the vinyl chloride monomer had an acidity of 2.6 parts per million calculated as hydrogen chloride as shown by titration of a 100 millimeter sample in methanol. After two minutes contact with mossy zinc the vinyl chloride had an acidity of 0.34 parts per million. After 55 minutes contact with the mossy zinc the acidity was 0.15 part per million.

Zinc metal is obtainable in several different grades having a purity of from 98 percent zinc to 99.9 percent zinc. The lower purity grades are brittle and form a dust which may be a source of contamination of the vinyl chloride. The high purity is ductile and is not fragile. While many of these grades of zinc may be used with proper filtration of the vinyl chloride monomer to remove dust or particles that may be suspended in the vinyl chloride it is preferred to use the high purity grade.

The example illustrating the process shows using the zinc with the monomeric vinyl chloride in liquid form. If desired a bed of zinc pellets can be made and the vinyl chloride passed through the bed in gaseous form. Other embodiments of the process will occur to those familiar with this art.

While certain representative embodiments and details have been shown for the purpose of illustrating the invention it will be apparent to those skilled in this art that various changes and modifications may be made therein without departing from the spirit or scope of the invention.

What we claim is:

1. The method which consists of contacting monomeric vinyl chloride with the zinc metal for a time sufficient for impurities in the vinyl chloride to react with said zinc metal to form an zinc compound and remove the impurity from the vinyl chloride.

2. The method of claim 1 in which the inpurity in the vinyl chloride is selected from the group consisting of hydrogen chloride and oxygen.

3. The method in claim 1 in which the impurity in the vinyl chloride is hydrogen chloride.

4. The method of claim 1 in which the impurity in the vinyl chloride is oxygen.

5. The method of claim 1 in which the zinc is in the form of particles of mossy zinc.

* * * * *